(12) United States Patent
Gurewich et al.

(10) Patent No.: US 7,837,992 B2
(45) Date of Patent: Nov. 23, 2010

(54) C-1 INHIBITOR PREVENTS NON-SPECIFIC PLASMINOGEN ACTIVATION BY A PROUROKINASE MUTANT WITHOUT IMPEDING FIBRIN-SPECIFIC FIBRINOLYSIS

(75) Inventors: Victor Gurewich, Cambridge, MA (US); Ralph Pannell, Brighton, MA (US)

(73) Assignee: Beth Israel Deaconess Medical Center, Boston, MA (US)

( * ) Notice: Subject to any disclaimer, the term of this patent is extended or adjusted under 35 U.S.C. 154(b) by 130 days.

(21) Appl. No.: 11/732,620

(22) Filed: Apr. 4, 2007

(65) Prior Publication Data

US 2007/0298023 A1 Dec. 27, 2007

Related U.S. Application Data

(63) Continuation-in-part of application No. 11/472,607, filed on Jun. 22, 2006, now abandoned.

(51) Int. Cl.
*A61K 38/48* (2006.01)
*C12N 9/72* (2006.01)
*C12N 9/68* (2006.01)

(52) U.S. Cl. .................. 424/94.64; 435/215; 435/217

(58) Field of Classification Search ............... 435/215, 435/217; 424/94.64
See application file for complete search history.

(56) References Cited

U.S. PATENT DOCUMENTS

| | | | |
|---|---|---|---|
| 5,055,295 A | 10/1991 | Welzel et al. | 424/94.2 |
| 5,472,692 A | 12/1995 | Liu et al. | |
| 5,626,841 A | 5/1997 | Gurewich | 424/94.63 |
| 5,759,542 A | 6/1998 | Gurewich | 424/94.64 |
| 5,866,358 A | 2/1999 | Brandazza et al. | 435/69.1 |
| 6,364,893 B1 | 4/2002 | Sahatjian et al. | 606/194 |
| 6,409,716 B1 | 6/2002 | Sahatjian et al. | 604/509 |
| 6,759,042 B2 | 7/2004 | Higazi | 424/130.1 |
| 2005/0031607 A1* | 2/2005 | Gurewich et al. | 424/94.64 |

OTHER PUBLICATIONS

De Zwaan et al. "Continuous 48-h C1-inhibitor treatment, following reperfusion therapy, in patients with acute myocardial nfarction" European Heart Journal (2002) 23, 1670-1677.*
Gregorek et al. "Concentration sf C1 Inhibitor in Sera of Healthy Blood Donors as Studied by Immunoenzymatic Assay" Complement and Inflammation 8(5-6), 1991, pp. 310-312.*
Eric Eldering et al. "Expression of Functional Human C1 Inhibitor in COS Cells" The Journal of Biological Chemistry vol. 263, No. 24, Issue of Aug. 25, pp. 11776-11779,1988.*
AG Fennerty et al., Chest. 95: 88S-97S (Feb. 1989).
Z. Sun et al. J Biol Chem. 272: 23818-23823 (Sep. 19, 1997).
JN Liu et al. Circ Res. 90: 757-763 (Apr. 19, 2002).
V. Gurewich et al., J Thromb Haemost. 4: 1559-65 (Jul. 2006).
Pannell and V. Gurewich, Blood. 69:22-26 (Jan. 1, 1987).
R. Pannell and V. Gurewich, Blood. 67:1215-1223 (May 1, 1986).
G. Murano et al. Blood 55: 430-436 (Mar. 1, 1980).
AK Rao et al., J Amer Coll Cardiol. 11: 1-11 (Jan. 1, 1988).
Bennett et al., J Amer Coll Cardiol. 10: 627-632 (Sep. 1987).
Huisman et al., Thromb Haemost. 73: 466-471 (1995).
JN Liu et al., Biochemistry 35: 14070-14076 (Nov. 12,1996).
JN Liu and V. Gurewich, J Clin Invest. 88: 2012-2017 (1991).
JN Liu and V. Gurewich, Biochemistry 31: 6311-6317 (Jul. 14, 1992).
Pannell et al., J Clin Invest. 81: 853-859 (Mar. 1988).
Badylak et al., J. Pharmacological Methods, 19: 293-304 (Jul. 1988).
M. Montoney et al., Circulation 91: 1540-1544 (Mar. 1995).
Armstrong et al., Circulation 107: 2533-2537 (May 2003).
Owen et al., Blood. 72: 616-620 (Aug. 1988).
Rapold et al., Blood 77: 1020-1024 (Mar. 1991).
Harpel et al., Jo Biol Chem 260: 4432-4440 (Apr. 10, 1985).
Hoylaerts et al., J Biol Chem. 257: 2912-2919 (Mar. 1982).

(Continued)

*Primary Examiner*—L. Blaine Lankford
*Assistant Examiner*—Thane Underdahl
(74) *Attorney, Agent, or Firm*—Medlen & Carroll, LLP

(57) ABSTRACT

A mutant prourokinase plasminogen activator (M5) was developed to make prouPA less subject to spontaneous activation during fibrinolysis. C1-inhibitor complexes with tcM5. The effect of C1-inhibitor on fibrinolysis and fibrinogenolysis by M5 was determined. Supplemental C1-inhibitor restores the stability of M5 but not that of prouPA. Clot lysis by M5 with supplemental C1-inhibitor showed no attenuation of the rate of fibrinolysis, whereas fibrinogenolysis was prevented by C1-inhibitor. Due to higher dose tolerance of M5 with C1-inhibitor, the rate of fibrin-specific lysis reached that achievable by nonspecific fibrinolysis without inhibitor. Plasma C1-inhibitor stabilized M5 in plasma by inhibiting tcM5 and thereby non-specific plasminogen activation. At the same time, fibrin-specific plasminogen activation remained unimpaired. This unusual dissociation of effects has significant implications for improving the safety and efficacy of fibrinolysis. Methods of reducing bleeding and non-specific plasminogen activation during fibrinolysis by administering M5 along with exogenous C1-inhibitor are disclosed.

10 Claims, 5 Drawing Sheets

OTHER PUBLICATIONS

C. De Zwaan et al., European Heart Journal 23: 1670-1677 (Nov. 2002).

H. Gregorek et al., Complement Inflamm. 8: 310-2 (1991).

Gurewich et al., "Effective and Fibrin-specific Clot Lysis by a Zymogen Precursor Form of Urokinase (Pro-urokinase)", *J. Clin. Invest.*, . 73,:1731-1739 (1984).

Heckel et al., "Prediction of the Three Dimensional Structure of the Enzymatic Domain of the t-PA", *J. Comp. Aided Mol. Des.*, 2: 7-14 (1988).

Liu et al., "Inactivation of the Intrinsic Activity of Pro-urokinase by Diisoprophyl Fluorophosphate is Reversible", *J. Biol. Chem.*, 270(15), 8408-8410 (1995).

Gurewich et al., New Therapeutic Agents in Thronmbosis and Thrombolysis, 2$^{nd}$ edition, chap 36, "A mutant form of prourokinase that spares hemostatic fibrin," A.A. Sasahara and J. Loscalzo, eds., Marcel Dekker, Inc, NY, pp. 583-592, 2003, rec'd at the NIH Natl Library of Medicine, Bethesda, MD on Dec. 10, 2002.

Yuming et al., "High-Level Expression and Purification of Human Pro-UK cDNA in *Escherichia coli*", *Chinese Journal of Biotechnology*, 13(4): 233-238 (1998).

Nienaber et al., "Conformational Similiarities between One-Chain and Two- Chain Tissue Plasminogen Activator (t-PA): Implications to the Activation Mechanism on One-Chain t-PA", *Biochem.*, 31: 3852-3861 (1992).

Parsons et al., "Diffusion-and-Perfusion-weighted MRI Response to Thronbolysis in Stroke", *Ann Neurol* 51(1): 28-37 (2001).

Barnwell et al., "Safety and Efficacy of Delayed Intraarterial Urokinase Therapy with Mechanical Clot Disruption for Thromboembolic Stroke", *Am J Neuroradiology*, 15(10): 1817-1822 (1994).

Orsini et al., "Efficient Renaturation and Fibrinolytic Properties of Prourokinase and a Deletion Mutant Expressed in *Escherichia coli* as Inclusion Bodies", *Eur. J. Biochem.*, 195, : 691-697 (1991).

Peterson et al, "Quenching of the Amidolytic Activity of One-Chain Tissue-Type Plasminogen Activator by Mutation of Lysine-416", *Biochem.*, 29: 3451-3457 (1990).

Verde et al., "Identification and Primary Sequence of an Unspliced Human Urokinase Poly(A)' RNA", *Proc. Natl. Acad. Sci.*, 81: 4727-4731 (1984).

Smith, "In vitro mutagenesis," *Am. Rev. Genet* 19:423-462 (1985).

Mandel et al., "Calcium-dependent bacteriophage DNA infection," *J. Mol. Biol.* 53:159-162 (1970).

Kunkel , "Rapid and efficient site-specific mutagenesis without phenotype selection," *Proc. Natl. Acad. Sci.*, 82: 488-492 (1985).

Studier et al., "Use of bacteriophage T7 RNA polymerase to direct selective high-level expression of cloned genes," *J. Mol. Biol.* 189:113-130 (1986).

Studier et al., "Use of T7 RNA polymerase to direct expression of cloned genes," *Meth. Ezymol* 185:60-89 (1990).

* cited by examiner

C-1 INHIBITOR PREVENTS NON-SPECIFIC PLASMINOGEN ACTIVATION BY A PROUROKINASE MUTANT WITHOUT IMPEDING FIBRIN-SPECIFIC FIBRINOLYSIS

RELATED APPLICATIONS

This application is a continuation-in-part of prior U.S. application Ser. No. 11/472,607, filed Jun. 22, 2006, herein incorporated by reference.

BACKGROUND OF THE INVENTION

Existing thrombolytic drugs, used in the treatment of thromboembolic diseases, have limited effectiveness and also carry the risk of rethrombosis and hemorrhagic complications. Clinical experience with plasminogen activators has highlighted problems with both efficacy and side effects, particularly hemorrhage [Rao et al. J Amer Coll Cardiol. 11: 1-11 (1988); Fennerty et al. Chest. 95: 88S-97S (1989)]. Because both endpoints are dose-related, the efficacy of therapeutic thrombolysis has always been handicapped by its side effects.

Currently most therapeutic thrombolysis is performed using tissue plasminogen activator (tPA) and its derivatives. TPA can have hemorrhagic side effects. For example, tissue plasminogen activator (tPA) at a dose of 150 mg has been shown to induce superior coronary thrombolysis, but has been accompanied by an unacceptable incidence of intracranial hemorrhage, obliging the adoption of a less effective dose of 100 mg [Braunwald et al. J Amer Coll Cardiol. 9: 467 (1987); Grossbard. J Amer Coll Cardiol. 9:467 (1987)].

Similarly, the other natural plasminogen activator, single-chain urokinase plasminogen activator (prouPA), a proenzyme, requires high infusion rates for effective coronary thrombolysis which causes plasminemia and results in conversion of single to two-chain uPA (tcuPA) and bleeding [Meyer et al. Lancet 1:863-868 (1989)].

The bleeding complications of therapeutic thrombolysis have been ascribed to the direct lysis of hemostatic fibrin at a vascular injury site and to the hemorrhagic diathesis caused by non-specific plasmin generation resulting in fibrinogenolysis, degradation of fibrinogen and of clotting factors V and VIII. Fibrinogen is the principal protein constituent of a fibrin clot; clotting factor V is a cofactor in the coagulation system, the lack of which causes a predisposition for hemorrhage; and clotting factor VIII is an essential clotting factor, the lack of which causes Hemophilia A.

Both tPA and prouPA are fibrin-specific in that they preferentially activate plasminogen bound to fibrin over free plasminogen. At physiological concentrations, plasminogen activation by tPA and prouPA is fibrin-dependent and confined to the clot environment by plasma inhibitors. But, at therapeutic concentrations, the fibrin selectivity of tPA and prouPA is compromised, largely due to the fact that these concentrations are in excess of inhibitors, particularly plasminogen activator inhibitor-1 (PAI-1), their principal plasma inhibitor. The intrinsic activity of prouPA at therapeutic concentrations was sufficient to activate plasma plasminogen, which converted single-chain prouPA to two-chain uPA (tcuPA). Since tcuPA is a non-specific plasminogen activator, the fibrin-specificity of prouPA is lost. Thus prouPA's specificity depends on its plasma stability which allows tcuPA and plasmin generation to be confined to the fibrin clot [Pannell and Gurewich, *Blood*, 67: 1215-1223 (1986)]. The systemic activation of plasma plasminogen results in the generation of systemic tcuPA and undermines the therapeutic use of prouPA.

At therapeutic concentrations, prouPA is especially vulnerable to non-specific plasmin generation since this results in loss of its proenzyme configuration due to its conversion to tcuPA, a non-specific activator, which, being an enzyme, then amplifies systemic plasmin generation several hundred fold.

This cycle of reactions is initiated by the relatively high intrinsic activity of prouPA which at therapeutic concentrations triggers plasminogen activation. Therefore, a prouPA mutation (M5) with a lower intrinsic catalytic activity was developed. A five-fold reduction in intrinsic activity was achieved by a site-directed single residue exchange on a flexible loop in the catalytic domain (Lys3000→His) of prouPA [Liu, et al. Biochemistry 35: 14070-14076 (1996)]. This produced a corresponding degree of improvement in plasma stability or inertness at therapeutic concentrations. Unexpectedly, after activation to two-chain M5 (tcM5), the mutant had a two-chain activity almost twice that of tcuPA [Sun et al., *J Biol. Chem.* 272: 23818-23823 (1997)], consistent with their two-chain active catalytic sites also being functionally distinct. U.S. Pat. No. 5,472,692 describes prouPA mutants and the disclosure is incorporated herein by reference.

M5 induced efficient, fibrin-specific clot lysis in a plasma milieu in vitro and in dogs with venous thromboemboli in which M5 was associated with no more bleeding than placebo [Liu et al. Circ Res. 90: 757-763 (2002)] In a second animal study of M5, a more challenging arterial thrombus was selected and M5 was administered by a bolus/infusion administration modeled on the clinical administration of prouPA or tPA. Because blood loss from injury sites was the side effect of most concern, a more quantitative measure of blood loss was used. Furthermore, the plasma inhibition of tcM5 was studied and found to be related to a plasma inhibitor novel for tcuPA. M5 and tPA induced comparably effective lysis, but blood loss from fresh hemostatic sites was ten-fold higher with tPA, suggesting that M5 spared hemostatic fibrin at doses which lyse intravascular clots [Pannell et al. Blood. 69: 22-26 (1987)]. A difference in the lytic sensitivities of hemostatic versus intravascular fibrin to M5 was related to differences in the mechanisms of fibrin-dependent plasminogen activation by the two activators [Gurewich et al. J Thromb Haemost. 4: 1559-65 (2006)]. Specifically, M5 selectively activated plasminogen on partially degraded (fibrin fragment E) and not on intact fibrin, whereas tPA targeted plasminogen on intact fibrin (fibrin fragment D) [Liu et al. J Clin Invest. 88: 2012-2017 (1991)], which corresponds to hemostatic fibrin. However, a novel, additional explanation for the low bleeding rate with M5 also came to light in this study [Gurewich et al. J Thromb Haemost. 4: 1559-65 (2006)].

Zymography of plasma samples from dogs in the dose-finding phase in which higher infusion rates of M5 were used, and where non-specific activation occurred, showed an unusual inhibitor complex with tcM5. This complex was also seen when tcM5 (but not M5) was incubated in vitro in dog or human plasma. The inhibitor was identified as C1-inhibitor based on its co-migration with a complex formed with purified C1-inhibitor and Western blotting with specific antibodies. It was postulated that endogenous C1-inhibitor helped confine tcM5 activity to the fibrin-clot environment, thereby limiting non-specific plasminogen activation and sparing hemostatic fibrin in these dogs [Gurewich et al. (2006), supra]. In the present study, C1-inhibitor inhibition of tcM5 was further investigated and its effect on fibrin-specific and non-specific plasminogen activation by M5 was characterized in vitro.

SUMMARY OF THE INVENTION

ProuPA is unstable in plasma at therapeutic concentrations. A mutant form, M5, was developed to make prouPA less subject to spontaneous activation in plasma during fibrinolysis. The spontaneous activation to tcuPA preempted prouPA-mediated fibrinolysis at therapeutic concentrations and seriously compromised prouPA in clinical trials.

Activation of M5 to tcM5 induced a higher catalytic activity than tcuPA, implicating an active site functional difference. Consistent with this, an unusual tcM5 complex with plasma C1-inhibitor was recently described in dog and human plasma. The effect of C1-inhibitor on fibrinolysis and fibrinogenolysis by M5 is the subject of this study.

Zymograms of tcM5 or tcuPA incubated in plasma revealed prominent tcM5:C1-inhibitor complexes which formed within five minutes. The inhibition rate by purified human C1-inhibitor (250 µg/ml) was about seven-fold faster for tcM5 than for tcuPA (10 µg/ml), and several-hundred fold faster than for tPA, an interaction that was previously reported [Huisman et al. Thromb Haemost. 73: 466-471 (1995)]. C1-inhibitor's effect on the stability of M5 or prouPA was determined by incubating them in plasma at high concentrations (10-20 µg/ml) with and without C1 inhibitor supplementation. Above 10 µg/ml, depletion of all plasma plasminogen occurred, indicating plasmin generation and tcM5/tcuPA formation. With supplemental C1-inhibitor, the stability of M5 was restored but not that of prouPA. Clot lysis by M5 with or without supplemental C1-inhibitor showed no attenuation of the rate of fibrinolysis, whereas fibrinogenolysis was prevented by C1-inhibitor. Furthermore, due to higher dose tolerance of M5 with C1-inhibitor, the rate of fibrin-specific lysis reached that achievable by nonspecific fibrinolysis without inhibitor. Plasma C1-inhibitor stabilized M5 in its proenzyme configuration in plasma by inhibiting tcM5 and thereby non-specific plasminogen activation. At the same time, fibrin-specific plasminogen activation remained unimpaired. This unusual dissociation of effects by this plasminogen activator:inhibitor interaction is unprecedented and has significant implications for improving the safety and efficacy of fibrinolysis.

A number of related aspects are described in detail in the following sections.

DETAILED DESCRIPTION OF THE INVENTION

Figure 1:
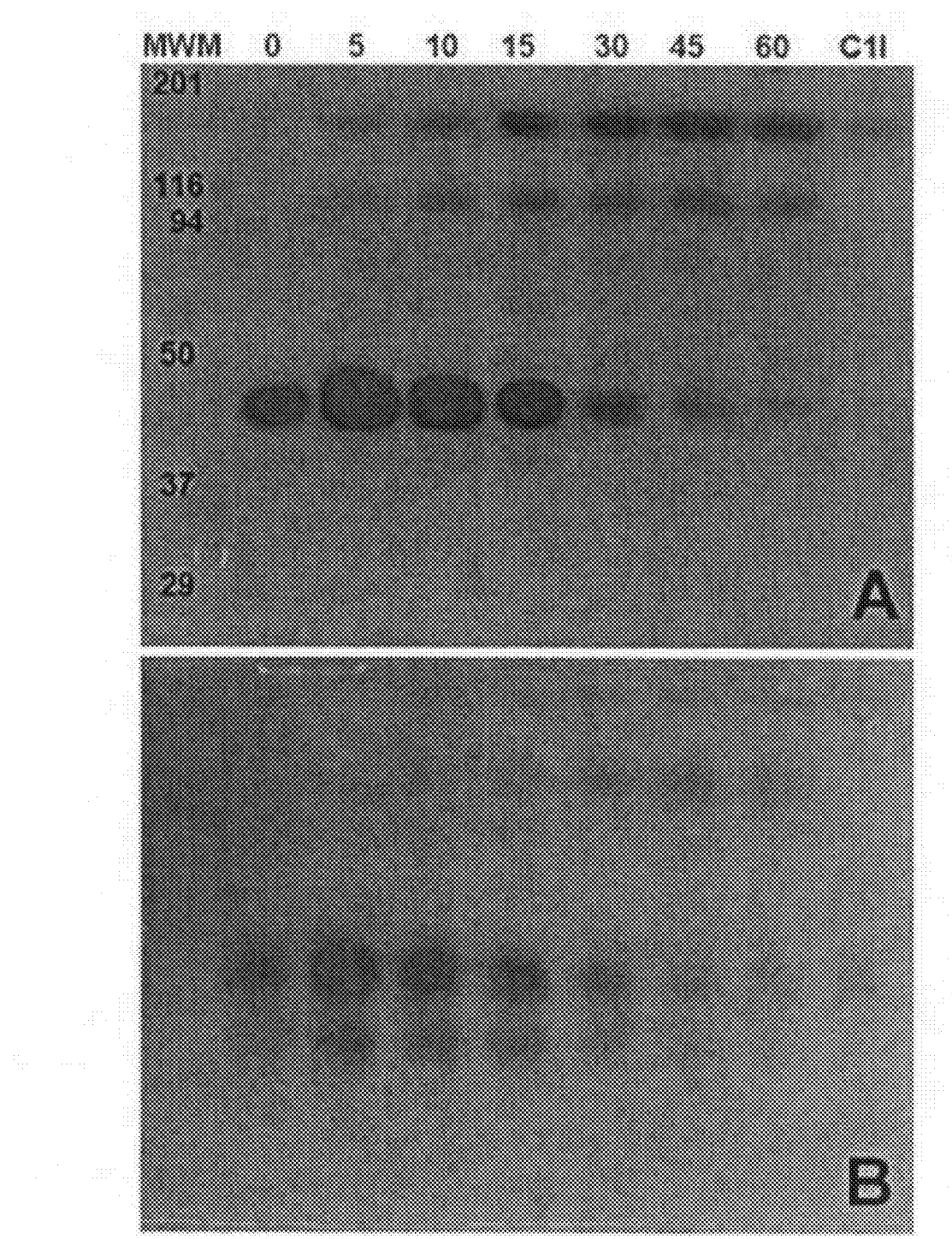
FIG. 1. Zymograms of tcM5 (5 µg/ml) (A) or tcuPA (5 µg/ml) (B) incubated in pooled bank plasma for 0-60 min. The inhibitor complex at the top, forming within 5 min with tcM5, corresponds to C1 inhibitor, as evidenced by the last lane (C1 I) of an incubation (60 min) mixture of purified C1-inhibitor (250 µg/ml) and tcM5 or tcuPA. With tcuPA (B) there is more free enzyme seen and the complex is barely visible, reflecting its slower inhibition rate compared with tcM5 (A). The second plasma inhibitor appearing at ~115 kDa corresponds to antithrombin, a known inhibitor of tcuPA.

The present invention relates to a novel method of reducing bleeding during fibrinolysis treatment and improving the rate of clot lysis. The method is based on the discovery that C1-inhibitor has the ability to inhibit plasminemia by inhibiting the two-chain prourokinase plasminogen activator mutant tcM5. The inhibition rate of this interaction is sufficient to prevent non-specific plasminogen activation but not fibrin-specific plasminogen activation.

ProuPA is a thrombolytic drug with the undesirable side effect of being vulnerable to spontaneous activation in plasma during therapeutic fibrinolysis. M5 is a single site mutant of prouPA developed to limit this non-specific effect and thereby to make fibrinolysis more fibrin-specific and to allow the physiological properties of prouPA to be retained at therapeutic doses. The plasminogen activator, M5, differs from the primary sequence of prouPA by a single amino acid substitution at position 300, where the amino acid Lysine has been replaced by Histidine (Lys 300→His) in a flexible loop region within the catalytic domain of single-chain prouPA. This residue exchange lowered the activator's intrinsic, single-chain activity by five-fold and made it more stable in plasma to a corresponding degree [Liu, et al. (1996), supra]. After plasmin-activation to tcM5, the catalytic activity of tcM5 was found to be higher than that of tcuPA [Sun et al. J Biol. Chem. 272: 23818-23823 (1997)], implicating an unanticipated functional difference in their two-chain catalytic sites as well. The present findings, that C1-inhibitor quenches the activity of tcM5 significantly more effectively than that of tcuPA, are consistent with such a difference, but were entirely unanticipated since no differences in inhibition by plasminogen activator inhibitor-1 (PAI-1) had previously been found.

C1-inhibitor is previously unknown as a plasma inhibitor of tcuPA. C1-inhibitor is a 104 kDa serine protease inhibitor with a normal plasma concentration of about 250 µg/ml and a half life of about 28 hours. Deficiency of this protein has been associated with a disease called hereditary angioedema. C1-inhibitor has long been administered clinically for the treatment of hereditary angioedema.

As discussed in the Background of the Invention section, ProuPA is a plasminogen activator that is subject to spontaneous activation in plasma at therapeutic concentrations due to its relatively high intrinsic catalytic activity. Plasmin then converts prouPA into tcuPA. Since tcuPA is a non-specific plasminogen activator, non-specific plasmin generation results in non-specific conversion of prouPA to tcuPA and loss of prouPA's physiological fibrin-specificity and associated properties. This includes the selective activation of plasminogen bound to partially degraded fibrin clots rather than intact fibrin clots, the latter corresponding to hemostatic fibrin. M5 has only one-fifth the intrinsic catalytic activity of prouPA and therefore retains its proenzyme form at therapeutic concentrations, and when used to lyse intravascular blood clots, M5 largely spares hemostatic fibrin, since this corresponds to intact fibrin. For the present invention, experiments were performed in vitro in human plasma. The actions of M5 were studied in comparison to prouPA, its parent molecule, and tPA, currently the most commonly used thrombolytic drug.

The serine proteases tPA and prouPA are both natural plasminogen activators, and both induce fibrin-specific lysis at limited doses by preferentially activating fibrin-bound plasminogen over free plasminogen. However, distinctly different mechanisms are responsible for this phenomenon. Each activator targets a different fibrin-bound plasminogen. The activator tPA is a single-chain enzyme with a high affinity for a specific binding site on fibrin, where tPA forms a ternary complex with an adjacent plasminogen [Hoylaerts et al., *J Biol. Chem.* 257: 2912-2919 (1982)]. This plasminogen is bound to an internal lysine binding site (Lys-157) in the Aα chain of the D-region of fibrin [Nieuwenhuizen W et al., *Biochim Biophys Acta.* 748: 86-92 (1983)]. In the presence of fibrin fragment D binding site, which is constitutive of intact fibrin, plasminogen activation by tPA is promoted by as much as 1,000-fold [Petersen et al., *Biochim Biophys Acta.* 952: 245-254 (1988)], reflecting the importance of the ternary complex with intact fibrin for tPA.

By contrast, the single-chain prouPA has no fibrin affinity. Yet when a clot is added to plasma containing prouPA (or M5), local activation of a fraction of the prouPA takes place on the fibrin surface and lysis is triggered [Liu et. al., *Biochemistry* 35: 14070-14076 (1996)]. This sequence of events is facilitated by a conformational change in plasminogen for which prouPA (or M5) has high substrate affinity. This change occurs when plasminogen binds to its carboxy-terminal lysine binding site in the E region of fibrin. In the presence of fibrin fragment E, plasminogen activation by single-chain prouPA/M5 is equal to that of its two-chain derivative, tcuPA or tcM5, corresponding to a several hundred-fold promotion of its intrinsic activity [Liu and Gurewich, *Biochemistry* 31: 6311-6317 (1992)].

Therefore, tPA and prouPA/M5 induce fibrin dependent plasminogen activation involving selectively different fibrin-bound plasminogen moieties. In the case of tPA, it is dependent on an internal lysine plasminogen binding site in the fibrin D region, whereas prouPA/M5 is dependent on carboxy-terminal lysine binding in the E region of fibrin. This difference is selective since there is little or no reciprocity. In a purified system, plasminogen activation by tPA is promoted specifically by fibrin fragment D and that by prouPA/M5 is promoted only by fibrin fragment E (Liu and Gurewich, *J Clin Invest.* 88: 2012-2017 (1991)). Newly formed intact (hemostatic) fibrin contains only the internal lysine plasminogen binding site in the D region of fibrin. The carboxy-terminal lysines in the E region are created only after plasmin degradation has occurred (Harpel et al., *J Biol. Chem.* 260: 4432-4440 (1985)). This difference is evidenced by the lag phase which is characteristic of prouPA (or M5)-induced clot lysis in a plasma milieu and by the fact that the lag phase is substantially attenuated by gentle pre-treatment of the clot with plasmin, which creates the fibrin fragment E carboxy-terminal lysine plasminogen binding sites. Conversely, tPA-induced clot lysis in plasma has no lag phase and tPA lyses intact and degraded fibrin clots equally well under these same conditions (Pannell et al., *J Clin Invest.* 81: 853-859 (1988)). Thus, intact fibrin is relatively resistant to lysis by prouPA/M5 whereas it is not resistant to tPA.

Hemostatic fibrin, consistent with its physiological function, is protected from plasmin degradation by several physiological safeguards. These include the inhibition of free tPA (and tcuPA) by PAI-1 and the removal of carboxy-terminal binding sites on fibrin by thrombin-activated procarboxypeptidase in plasma (Hendriks et al., *J Clin Chem. Clin Biochem.* 27: 277-280 (1989)). By contrast, when an intravascular thrombus forms and causes a vascular occlusion, physiological mechanisms for its degradation are triggered. In particular, there is a release of tPA from the vessel wall which, aided by the local stasis, binds to the thrombus. Fibrin degradation is initiated thus creating new carboxy-terminal lysine plasminogen binding sites which facilitate lysis (Harpel et al., *J Biol. Chem.* 260: 4432-4440 (1985)), particularly by prouPA/M5.

The presence of the fibrin E region plasminogen binding sites in an intravascular thrombus but not in hemostatic fibrin provides an explanation for why effective thrombolysis by M5 spares hemostatic fibrin, but only if systemic tcM5 generation is avoided. In contrast, the D region ternary complex plasminogen binding site is present in hemostatic fibrin, making it more vulnerable to lysis by tPA. This concept is consistent with tPA-associated bleeding which has been shown to have a low correlation with fibrinogen degradation, a sign of non-specificity (Montoney et al., *Circulation* 91: 1540-1544 (1995)). This is because this bleeding is related to direct lysis of fibrin at a hemostatic site. By contrast, bleeding with prouPA is directly correlated with non-specificity, which leads to a generalized hemorrhagic state.

In a study of rebleeding from hemostatic sites during thrombolytic treatment of dogs, the findings of U.S. application Series No. 11/472,607 indicated a relative sparing of hemostatic versus intravascular fibrin when M5 was used and suggested that these two fibrins are functionally distinct with respect to their sensitivity to lysis by M5. In the study, M5 induced lysis was comparable in efficacy, but caused ten-fold less bleeding than tPA induced lysis, consistent with a sparing of hemostatic fibrin. The study further showed that when the enzymes tcM5 and tcuPA were each incubated in vitro in either human or dog plasmas, an inhibitor complex consistent with C1-inhibitor (~150 kDa) appeared within minutes of the incubation of tcM5 in plasma. The sparing of hemostatic fibrin was postulated to be both because plasminogen activation by M5 was not promoted by intact fibrin and because of the efficient inhibition of tcM5 by plasma C1-inhibitor, which prevented non-specific plasmin generation.

The present invention is concerned with the effect of C1-inhibitor on fibrinolysis and fibrinogenolysis by M5. As discussed in the Exemplification section which follows, C1-inhibitor formed the predominant complex with tcM5 in plasma (FIG. 1A), in contrast to the results with tcuPA, suggesting that C-1 inhibitor helps prevent non-specific plasmin generation by M5/tcM5. During thrombolysis, plasmin generation must be confined to the fibrin clot environment, if not, plasminogen in the ambient plasma will be activated and the proenzyme (M5 or prouPA) converted to the two-chain enzyme. Only plasma inhibitors can confine tcM5 (or tcuPA) activity to the clot environment. Plasma inhibitors are essential factors in the fibrin-specific mechanism of action of prouPA or M5 and for retaining the proenzyme state of prouPA and M5 in an environment in which plasminogen is present.

As discussed in the Exemplification section, tcM5 and tcuPA at identical concentrations were incubated with exogenous C1-inhibitor in plasma. The zymograms show a rapid and progressive loss of the tcM5 free enzyme associated with the appearance of prominent inhibitor complexes (FIG. 2A). In the present comparative study, tcM5 was more efficiently inhibited in plasma than tcuPA, mostly due to its formation of a complex with C1-inhibitor. Only a very faint C1-inhibitor complex with tcuPA was seen (FIG. 2B). There was essentially complete inhibition of tcM5 within 60 min, whereas 30% of the tcuPA activity remained even after 3 h of incubation. In a purified system, the inhibition rate of C1-inhibitor was about seven-fold greater against tcM5 than tcuPA. As shown in Table 1, the inhibition of tcuPA was about 100-fold faster than that previously described for tPA. The inhibition of tcM5 in plasma is what limits the cyclic reactions which would otherwise result in plasmin generation and lead to more tcM5 and plasmin generation, and bleeding. The efficient inhibition of tcM5 by C1-inhibitor can, therefore, contribute significantly to confining tcM5 generation to the intravascular clot environment, thereby protecting the more remote hemostatic fibrin.

Figure 4:
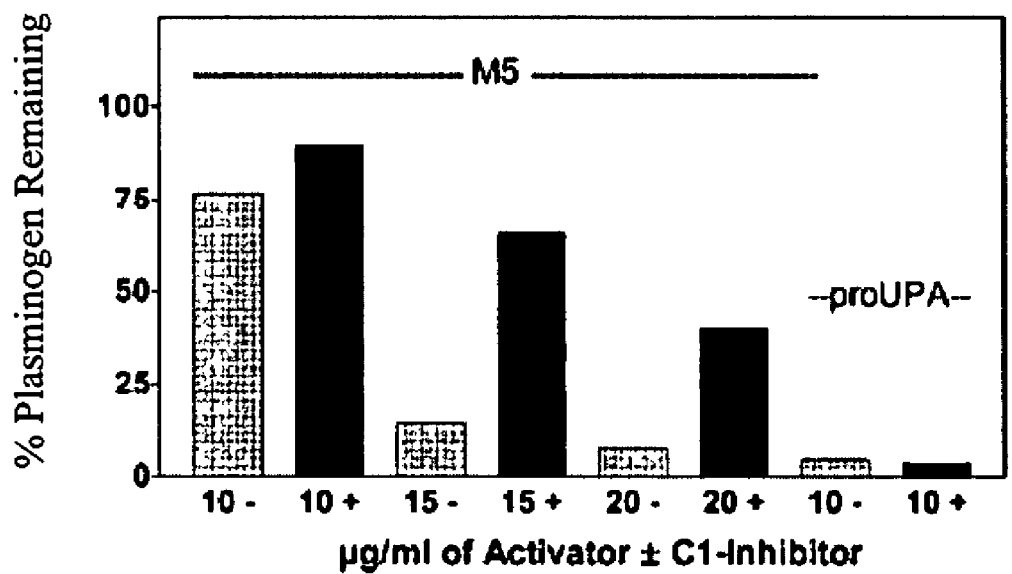
FIG. 4. The effect of C1-inhibitor (250 µg/ml) when added to bank plasma on plasminogen preservation in the presence of M5 (10, 15 or 20 µg/ml) or prouPA (10 µg/ml) incubated 4h in plasma. Plasma plasminogen remaining (% of baseline) is represented on the ordinate axis. As shown, supplementation (+) of the plasma with the inhibitor significantly reduced plasminogen depletion by M5 at all doses but not by prouPA at the dose used.

As discussed in the Exemplification section, when plasma was supplemented with C1-inhibitor (250 µg/ml), the M5 concentration threshold at which tcM5 conversion and non-specific plasminogen activation occurred was substantially raised (FIG. 4). Therefore, C1-inhibitor, by inhibiting tcM5, effectively helped stabilize M5 in plasma and allowed a higher concentration of M5 to be tolerated without compromising fibrin-specificity. By contrast, as shown by the last two bars in FIG. 4, C1-inhibitor supplementation had no attenuating effect on plasminogen activation of prouPA at the high concentrations used in these experiments.

Figure 5A:
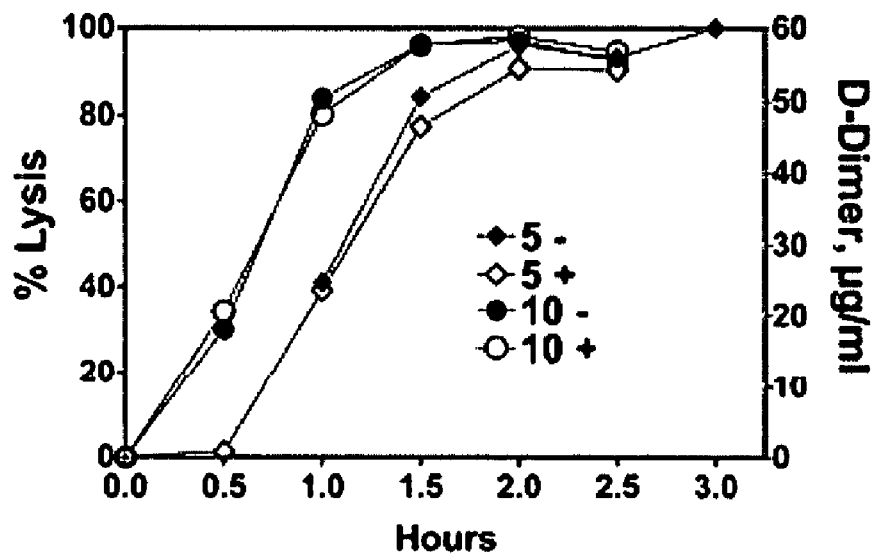
FIG. 5A. Lysis curves determined from release of D-Dimer from clots in a plasma milieu with (+) or without (−) supplemental C1-inhibitor (250 µg/ml) and containing S or 10 µg/ml M5. As shown, the presence of the inhibitor did not attenuate the rate of fibrinolysis.
Figure 5B:
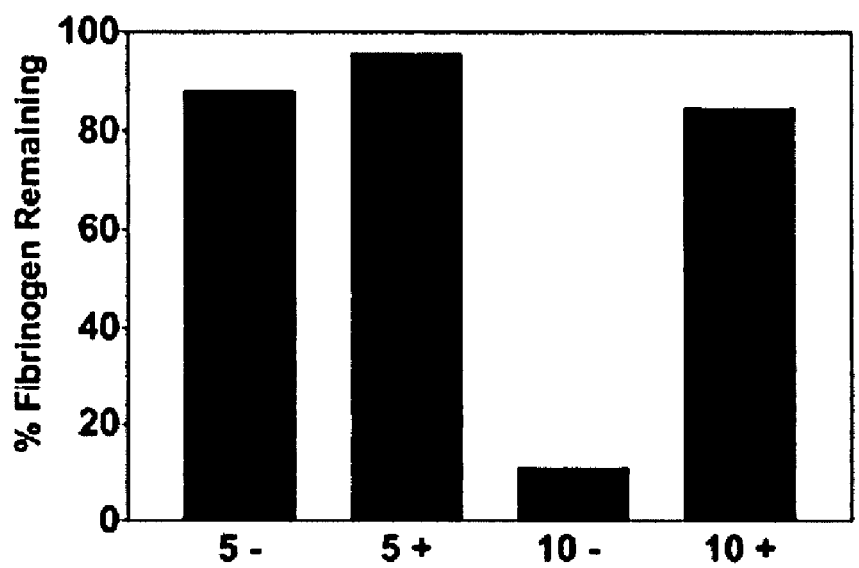
FIG. 5B. Fibrinogen concentrations remaining at the end of each clot lysis from 5A expressed as % of baseline. At 10 µg/ml of M5 (10−) there was loss of almost all the fibrinogen, reflecting its degradation. However, with supplemental C1 inhibitor (10+) this did not occur.

When fibrin-dependent plasminogen activation was tested by measuring the rate of clot lysis by M5, no inhibition by supplemental C1-inhibitor was observed (FIG. 5A). However, fibrinogenolysis, reflecting non-specific plasminogen activation, was completely prevented (FIG. 5B). This difference between the inhibition of non-specific plasminogen activation and fibrin-dependent plasminogen activation (fibrinolysis) was unexpected and unpredictable since previous studies with prouPA and supplemental PAI-1 showed that this inhibitor inhibited both reactions to a comparable degree.

These results of the present study make clear, and the present invention includes, methods of administering an amount of exogenous C1-inhibitor along with M5 during fibrinolysis treatment that limit non-specific plasminogen activation in the blood and reduce bleeding complications of thrombolytic therapy. An amount of M5 effective to cause lysis of an occlusive blood clot should be administered along with an amount of exogenous C1-inhibitor sufficient to limit non-specific plasminogen activation in blood. Moreover, since C1-inhibitor permits higher doses to be safely administered, faster rates of lysis are possible, as shown in FIG. 5A. The M5 mutant is administered as a thrombolytic agent in the same way as prouPA and tcuPA. M5 is mixed with a pharmaceutically acceptable carrier, e.g., saline, and administered by intravascular, e.g., intravenous or intra-arterial injection. The present invention includes methods where M5 may be injected as a bolus of approximately 20 to 60 mg, or may be infused intravenously at a rate of 40-80 mg/hour. Since M5 has far greater plasma stability than native prouPA and is less likely to induce non-specific plasminogen activation, higher dosages, e.g., infusions of up to 200 mg/hour may also be used.

In another embodiment, the present invention includes a method of inhibiting the enzymatic activity of tcM5. As is detailed in the Exemplification, an amount of exogenous C1-inhibitor sufficient to limit the formation of tcM5 from M5 activation should be administered to a patient desiring to limit the activity of tcM5.

In another embodiment, the present invention includes a method of increasing the plasma stability or inertness of M5 during fibrinolysis treatment. M5's stability is increased by administering exogenous C1-inhibitor sufficient to establish a C1-inhibitor concentration within the range of 1.5 to 4, preferably 2 to 3, times the concentration of average normal endogenous C1-inhibitor. The C1-inhibitor inhibits non-specific plasminogen activation of tcM5 without inhibiting clot lysis or fibrin-specific plasminogen activation by tcM5.

The present invention includes the treatment of a patient with M5 and an amount of exogenous C1-inhibitor sufficient to establish C1-inhibitor concentrations greater than physiological levels in the plasma of the patient. There is a range of normal physiological levels. Average normal physiological levels are about 250 µg/ml. Individuals at the lower end of the range, especially those being treated for ischemic stroke, may have physiological levels of C1-inhibitor as low as 150 µg/ml. Those in the high physiological range may have native levels of C1-inhibitor as high as 450 µg/ml. Those at the lower end would be more vulnerable to bleeding complications related to M5 and so their need for supplementation would be greater. The concentrations established in plasma during treatment should be within the range of 1.5 to 4, preferably 2 to 3, times that of average physiological levels or approximately 0.5 g/l to 1.5 g/l. As is detailed in the Exemplification section, a C-1 inhibitor supplementation of 0.25 g/l was effective in promoting the plasma stability of M5, raising the M5 threshold concentration at which non-specific plasminogen activation occurs, and significantly inhibiting the non-specific activity of tcM5.

At the same time that M5 fibrinolysis was not inhibited, fibrinogenolysis was completely inhibited by supplementation with C1-inhibitor. Therefore, C1-inhibitor restored fibrin-specificity to the more rapid clot lysis rate otherwise achievable only at non-specific doses of the activator, i.e., at which fibrin degradation by excess plasmin is the rate-limiting factor. As a result, the dose-limit for fibrin-specific clot lysis was raised. In fact, the rate achieved with supplemental C1-inhibitor was equivalent to that achievable by non-specific clot lysis, i.e., that rate possible when plasmin itself is rate limiting. Since all plasminogen activators lyse fibrin indirectly, the maximal rate of fibrinolysis possible is that at which plasmin degradation of fibrin becomes the rate limiting step in the lysis. C1-inhibitor supplementation made possible a maximal fibrinolysis rate by M5 in vitro without sacrificing fibrin-specificity. Therefore, the present invention also includes methods of accelerating the rate of clot lysis, during thrombolysis treatment in a patient, while preventing fibrinogen degradation. The methods include administering M5 in an amount sufficient to establish concentrations of 10-15 µg/ml in plasma together with exogenous C1-inhibitor in an amount sufficient to establish a concentration within the range of 1.5 to 4, preferably 2 to 3, times physiological levels in the plasma of the patient. The methods include the case wherein the level of C1-inhibitor established is about 500-750 µg/ml in the plasma of the patient.

The methods of the present invention include the administration of exogenous C1-inhibitor mixed with a pharmaceutically acceptable carrier and administered as a bolus wherein the level of C1-inhibitor in the plasma of the patient is brought into the high physiological range. Included is the method wherein the level of C1-inhibitor established in the plasma of the patient is about 750 µg/ml. The methods include administering the bolus of exogenous C1-inhibitor prior to thrombolysis with M5. The half-life of native C1-inhibitor is about 28 hours. That of recombinant C1-inhibitor can be much shorter, such as three hours. The appropriate amount of exogenous C1-inhibitor to administer depends on its half-life. A good quantity of exogenous C1-inhibitor to administer is 0.5 gm as a bolus or by intravenous infusion.

Native C1-inhibitor is used to treat hereditary angioedema. For the purposes of thrombolysis with M5, the longer half-life of native C1-inhibitor is not necessary because the C1-inhibitor is needed for at most 90 minutes. Therefore a recombinant C1-inhibitor may be used, including that made in yeast or *E. coli*. Recombinant forms may be non-glycosylated or glycosylated differently than the heavily glycosylated native C1-inhibitor. The differences in -glycosylation affect metabolism and may not be suitable for angioedema patients for which a long half-life may be optimal. However, thrombolysis is an acute therapy so that a much compromised half-life for C1-inhibitor would be well-suited for this application. C1-inhibitor enzymatic inhibition is determined by the protein rather than its glycosyl moiety. Both the native and the recombinant forms of C1-inhibitor can be used to inhibit tcM5 and thus accelerate the rate of blood clot lysis during thrombolysis while preventing fibrinogen degradation. Therefore the present invention includes methods wherein the exogenous C1-inhibitor administered is of recombinant origin or of native origin. The methods include the case wherein the exogenous C1-inhibitor is non-glycosylated or differently glycosylated from the native form.

C1-inhibitor also had a modest effect on non-specific plasminogen activation by prouPA/tcuPA, but only at much lower concentrations of them than those used in the present study. This is consistent with its weaker inhibition, which was, nevertheless, much greater than that reported for tPA [Huisman et al. Thromb Haemost. 73: 466-471 (1995)]. The principal plasma inhibitor of tPA and tcuPA is PAI-1. However, raised levels of PAI-1 have been associated clinically with impaired fibrinolysis [Juhan-Vague et al. Thromb Res. 33: 523-530 (1984); Meade et al. Lancet. 342: 1076-1079 (1993)]. Similarly, in studies of the effect of PAI-1 supplementation (25-100 ng/ml) on clot lysis by prouPA in a plasma milieu, a dose-dependent inhibition of clot lysis took place (unpublished observations). These previous findings with PAI-1 are in stark contrast to the present findings with C1-inhibitor, wherein clot lysis was not inhibited.

C1-inhibitor complexes were previously identified in the plasma of dogs given higher, non-specific doses of M5. It was postulated that this inhibition of tcM5 by endogenous C1-inhibitor may have contributed to the ten-fold lower blood loss associated with M5 compared with tPA in the study [Gurewich et al. (2006), supra]. The present findings indicate that if supplemental C1-inhibitor had been administered to these dogs, faster lysis rates from higher doses accompanied by the same low bleeding incidence would have been achieved.

The present invention includes a method of preventing side effects, such as bleeding, during fibrinolysis treatment in a patient by administering M5 along with exogenous C1-inhibitor. The M5 is administered in an amount sufficient to cause a maximal rate of lysis of an occlusive blood clot and the exogenous C1-inhibitor is administered in an amount sufficient to limit non-specific plasminogen activation by M5. The C1-inhibitor inhibits non-specific plasminogen activation and bleeding. The maximal rate of lysis is the rate at which the plasmin degradation of fibrin, rather than the plasminogen activation by M5, is the rate limiting step in clot lysis. Plasminogen activators, such as M5, are indirect lytic agents. They activate plasminogen which becomes plasmin. The plasmin then lyses fibrin. If the plasmin is the rate limiting step, the two-step reaction cannot go faster even if more plasminogen activator is added. Using supplemental C1-inhibitor allows the maximum rate of clot lysis by M5 to take place without risking massive non-specific plasminogen activation and its side effects. With M5 and C1-inhibitor, because of the action of C1-inhibitor on tcM5, the maximum rate of clot lysis can be achieved safely. C1-inhibitor prevents bleeding and at the same time allows for a more rapid rate of thrombolysis. In vivo the maximum rate of lysis can be achieved by M5 at a dose of about 150 mg infused over 60-90 minutes.

The methods of the present invention include methods of increasing the dose-range of fibrin-specific lysis by M5 in a patient. Included methods comprise administering exogenous C1-inhibitor in an amount sufficient to prevent non-specific plasminogen activation by M5. Included is the method wherein the exogenous C1-inhibitor administered establishes a concentration of C1-inhibitor, in the plasma of the patient, that is within the range of 1.5 to 4, preferably 2 to 3, times that of average normal physiological levels.

The dissociation observed between the inhibition by C1-inhibitor of nonspecific and fibrin-specific plasminogen activation is consistent with the two different rates of plasminogen activation which are involved. Fibrin bound plasminogen is activated more rapidly than free native plasminogen in plasma. In the case of prouPA/M5 it has been shown that plasminogen activation is promoted more than two-hundred. fold by fibrin, specifically fibrin fragment E [Liu et al. Biochemistry 31: 6311-6317 (1992)]. As a consequence, the C1-inhibitor inhibition rate of tcM5 is sufficient to prevent non-specific plasminogen activation but insufficient to interfere with the more rapid activation of fibrin-bound plasminogen.

In conclusion, C1-inhibitor was more reactive against tcM5 than tcuPA, and when added to plasma it prevented non-specific plasmin generation by M5 at high fibrinolytic concentrations. Since plasminemia can cause bleeding [Rao et al. (1988), supra; Fennerty et al. (1989), supra], clotting [Hoffmeister et al. Thromb Res. 103: S51-S55 (2001)], the "plasminogen steal" phenomenon [Torr et al. J Amer Coll Cardiol. 19: 1085-1090 (1992)], and complement activation

[Bennett et al. J Amer Coll Cardiol. 10: 627-632 (1987)], limiting non-specific plasmin generation without interfering with fibrinolysis is of special clinical interest. An inhibitor that controls this dose-related plasminogen activator side effect has the potential to optimize the lysis rate and minimize side effects, thereby helping overcome current limitations of therapeutic thrombolysis. Prevention of these consequences is unique to M5 with C1-inhibitor.

EXEMPLIFICATION

Materials

Recombinant Lys3000→His mutant (M5) prouPA expressed in *Escherichia coli* (*E. coli*) was prepared as previously described [Liu et al. (2002), supra] and obtained from Dr. Paolo Sarmientos at Primm (Milan, Italy). Recombinant prouPA expressed in *E. coli* was obtained from Landing Science and Technology Company, Nanjing, China. Human C1-inhibitor concentrate prepared from human plasma was kindly supplied by ZLB Behring GmbH (Marburg, Germany). Human Complement factor four (C4) was obtained from Calbiochem, Torry Pines, Calif. Chromogenic substrates for uPA (S-2444) and plasmin (S-2251) were obtained from DiaPharma (West Chester, Ohio, USA). The chromogenic substrate for C1 esterase (Spectrozyme C1E) was obtained from American Diagnostica, Stamford, Conn.

Methods

Fibrinogen was measured as thrombin clottable protein. Plasma was diluted with 2 vol 0.06 M sodium phosphate, pH 6.1. One volume of thrombin (100 NIH U/ml, ThromboMax from Sigma, St Louis, Mo., USA) was added, mixed, and incubated for 30 min at 37° C. The clot was wound onto a wooden stick to express the diluted serum, rinsed in 5 ml of the buffer, and deposited into a tube containing 1 ml of 5% NaOH. After boiling for 1 min, the clot was dissolved and the protein measured spectrophotometrically at 280 nm.

Zymography was performed by the method of Granelli-Piperno and Reich [J Exp Med. 148: 223-234 (1978)] as modified by Vassalli et al. [J Exp Med. 159: 1653-1658 (1984)] with sodium dodecyl sulfate polyacrylamide gel electrophoresis (SDS-PAGE) according to Laemmli. After electrophoresis, the gel washed with agitation for 2 h in 2.5% Triton X-100 in water, followed by 1 h in 0.1 M Tris-HCl (pH 8.0) and then placed on an underlay consisting of 0.8% agarose (Agarose low melting, Fisher Biotech, Kent City, Mich., USA), casein (2% w/v; Carnation non-fat dry milk, Nestle, Glendale, Calif., USA) and plasminogen (20 µg/ml) in 0.1 M Tris HCl (pH 8.0) With incubation, the electrophoretic bands of plasminogen activator produce a clear zone in the white casein. Plasminogen activator inhibitor complexes become active in this system and also show up as lytic zones.

Zymograms of the Two-Chain Activators in Plasma

The single-chain forms of M5 and of uPA were converted to two-chain by incubation with 0.2 µM plasmin (American Diagnostica, Greenwich, Conn., USA) for 45 min at 37° C. in 0.05 M Tris-HCl, 0.1 M NaCl, 0.010% Tween-80, 10 mg/ml BSA as previously described [Pannell et al. Blood. 69:22-26 (1987)]. These were added to human bank plasma (5 µg/ml) and incubated at 37° C. for 1 h with time point samples taken for zymography (FIG. 1).

Inhibitor Complexes in Plasma and with Purified C-Inhibitor

FIG. 1 shows zymograms of plasma in which equal amounts (5 µg/ml) of tcM5 (A) or tcuPA (B) were incubated (0-60 min). With tcM5 (A), there was a progressive loss over time of the uncomplexed enzyme associated with the appearance within 5 min and progressive increase of lysis bands at ~150 kDa, corresponding to complexes with C1-inhibitor. The last lane shows the complex which was formed when purified C1-inhibitor was incubated for 1 h with tcM5 (5 µg/ml) migrating in the same position With tcuPA (B), the uncomplexed enzyme persists in the plasma for a longer time and the C1-inhibitor complexes appear more slowly and are much less apparent. The complex with purified C1-inhibitor (last lane) is too faint to be visible on the print. The lower MW inhibitor complex in plasma (~115 kDa) is with antithrombin, a known plasma inhibitor of tcuPA [Murano et al. Blood 55: 430-436 (1980)]. This has about the same intensity as that with C1-inhibitor with tcuPA (but not with tcM5).

On the zymograms, both the free tcM5 but especially the tcuPA, appear as higher and lower molecular forms, the latter more degraded form is an inevitable by-product of the plasmin activation of their parent single-chain forms. Complexes with PAI-1 in the plasma are not visible due to the negligible concentration of this inhibitor relative to that of the activators.

C1-Inhibitor Inhibition of tcM5 and tcuPA

Figure 2:
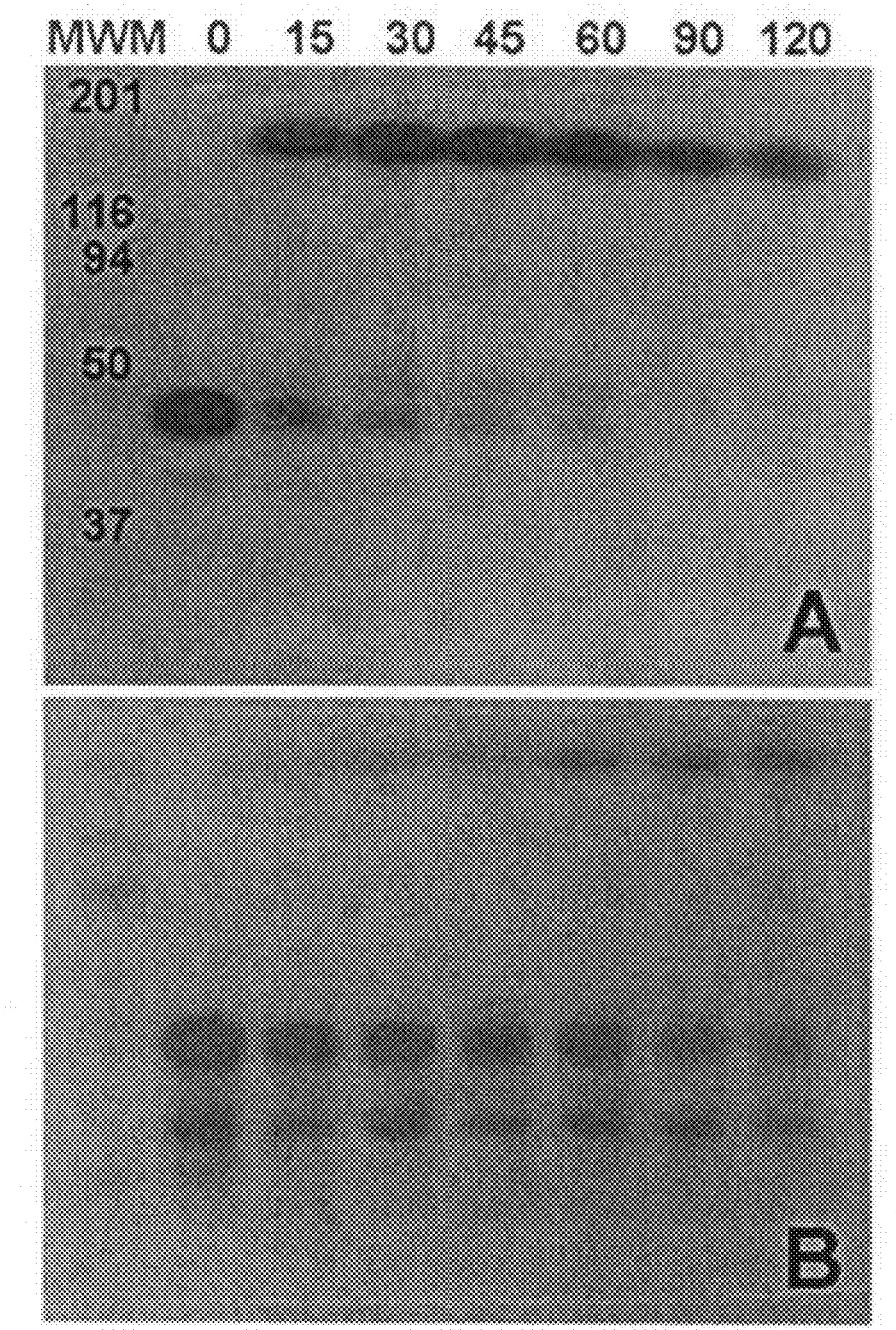
FIG. 2. Zymograms of 120 min incubation mixtures of 10 µg/ml tcM5 (A) or tcuPA (B) with purified C1-inhibitor (250 µg/ml). The more rapid inhibitor complexation by tcM5 corresponds to the more rapid quenching of activity shown in FIG. 3. The minor lower molecular weight lysis bands seen below the two enzymes correspond to by-products of the plasmin activation of the single chain proenzyme forms.

The two-chain forms of M5 and of uPA were incubated (10 µg/ml) with purified C1-inhibitor (250 µg/ml) at 37° C. in 0.05 M Tris-HCl, 0.1 M NaCl, 0.01% Tween-80, 10 mg/ml BSA. Samples were taken at time points and assayed for remaining activity by chromogenic assay (S-2444) (FIG. 2). The data were plotted directly (FIG. 3) and a non-linear regression for first-order logarithmic decay was performed using GraphPad Prism (version 3.03 for Windows, GraphPad Software, San Diego, Calif., USA) in order to obtain the half-life ($t_{1/2}$) for inhibition. The pseudo-first order inhibition rate constant was calculated from $k'=0.693/(t_{1/2} \times [tcuPA])$.

FIG. 2A and B are zymograms of incubation mixtures of equal amounts of tcM5 or tcuPA incubated in buffer in the presence of purified C1-inhibitor (250 µg/ml), corresponding approximately to its physiological concentration. Similar to the findings in plasma, a relatively rapid and progressive loss of the tcM5 free enzyme was seen associated with the appearance of prominent inhibitor complexes (FIG. 2A). By contrast, with tcuPA the free enzyme persisted due to only a modest formation of inhibitor complexes taking place during the incubation, reflecting the differences in their inhibition rates (FIG. 2B).

Kinetics of Inhibition by C1-Inhibitor

Figure 3:
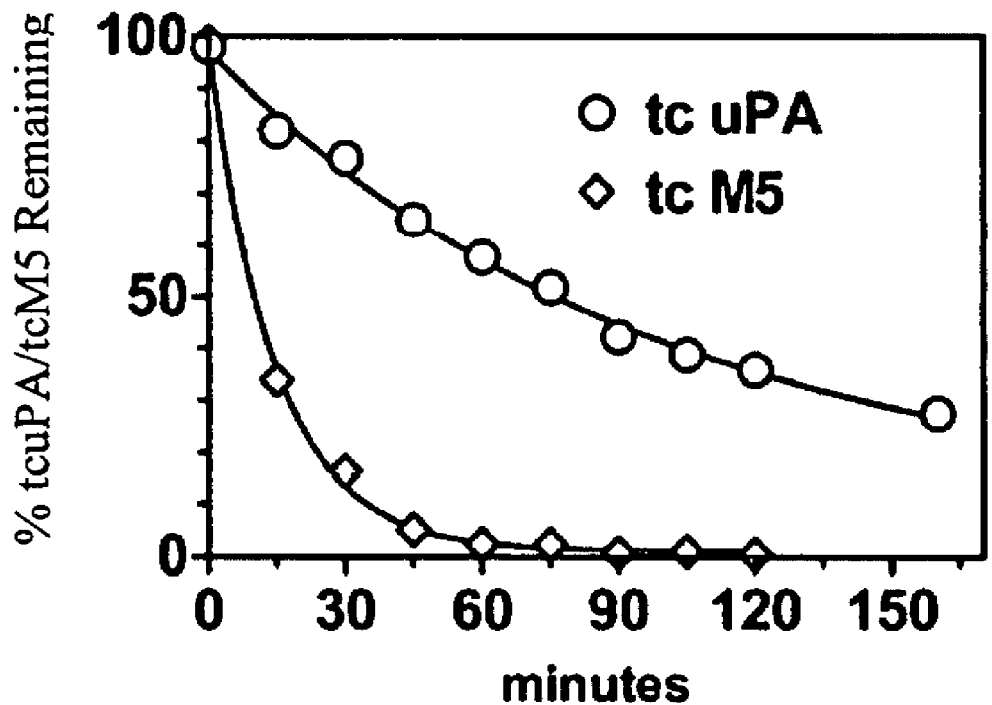
FIG. 3. The kinetics of tcM5 (diamonds) or tcuPA (circles) inhibition by C1-inhibitor from the incubation mixtures shown in FIG. 2. At the time points, uPA activity was measured with chromogenic substrate (S-2444). The points graphed are the means of two experiments (error bars are smaller than the symbols; the R2 of the curves was 0.987 for tcM5 and 0.997 for tcuPA). The data were fitted by computer to a non-linear regression for first order logarithmic decay.

FIG. 3 shows the kinetics of inhibition of tcM5 compared with tcuPA in buffer containing C1-inhibitor (250 µg/ml) and 10 µg/ml (a high therapeutic concentration) of the two activators. At time points, synthetic substrate (S-2444) activity was measured and expressed as percent of uPA activity remaining. As shown, inhibition of uPA activity occurred at two very different rates. There was essentially complete inhibition of tcM5 within 60 min, whereas 30% of the tcuPA activity remained even after 3 h of incubation.

TABLE 1

Inhibition Kinetics.

| | $t_{1/2}$ (min) | k' ($M^{-1} sec^{-1}$) |
|---|---|---|
| tcM5 | 10 | $5.78 \times 10^3$ |
| tcuPA | 68 | $0.85 \times 10^3$ |
| tPA[a] | | $0.008 \times 10^3$ |

[a]For melanoma single chain tPA from Murano et al., Blood 55: 430-436 (1980); adjusted to normalize to the inhibitor concentration we used.

The inhibition rate of C1-inhibitor was about seven-fold greater against tcM5 than tcuPA. Huisman et al. [Huisman et al. (1995), supra] previously reported that C1-inhibitor formed complexes with both single and two-chain tPA, but these complexes formed more slowly. C1-inhibitor has not previously been included among the plasma inhibitors of tcuPA [Murano et al. (1980), supra]. As shown in Table 1, the inhibition of tcuPA was about 100-fold faster than that previously described for tPA by Huisman et al. [Huisman et al. (1995), supra] (recalculated to normalize to the inhibitor concentration we used).

Stability of M5 or prouPA in Plasma as a Function of Supplemental C1-Inhibitor

To determine the stability of the single chain forms of M5 and uPA in plasma, the M5 and prouPA were incubated (37° C. for 4 h) in plasma at a range of concentrations (10, 15, and 20 µg/ml) with and without extra C1-inhibitor added (250 µg/ml). Enzymatic activation of plasminogen was determined by measuring the plasminogen remaining (FIG. 4) by chromogenic assay (S-2251) after its activation with Streptokinase (2500 units/ml). C1-inhibitor also inhibits plasmin [Harpel. J Clin Invest. 49(3): 568-75 (1970)] which potentially complicates the assay. However, it was determined that SK:plasmin complexes, which are generated for this assay, are not inhibited by C1-inhibitor (unpublished observations).

Since prouPA is far less stable in plasma than M5, a separate study using far lower concentrations (2 and 4 µg/ml) incubated in plasma 2 h and 4 h±C1-inhibitor was also performed.

Promotion of M5 Stability in Plasma by C1-Inhibitor Supplementation

M5, like prouPA, is a single-chain zymogen which is activated by plasmin. Plasmin generation is triggered by the intrinsic activity of the proenzymes when they reach a certain threshold, such as at therapeutic concentrations. Conversion to the two-chain forms then amplifies plasminogen activation. Although the intrinsic activity of M5 is five-fold lower than that of prouPA [Liu, et al. (1996), supra], making its plasma stability or inertness that much greater, it nevertheless also has its concentration limits.

Therefore, the effect, of supplemental C1-inhibitor (250 µg/ml) added to plasma, on the concentration threshold at which instability occurs was evaluated. M5 or prouPA (10, 15, and 20 µg/ml) were incubated in plasma for 4 h with or without additional C1-inhibitor, after which the plasma plasminogen remaining was measured.

As shown in FIG. 4, at an M5 concentration of 10 µg/ml, non-specific plasminogen activation began to occur (~25% loss of plasminogen) after 4 h, and at concentrations of 15 and 20 µg/ml, plasminogen activation by M5, as reflected by its depletion, was ~85% and >90% respectively. However, with additional C1-inhibitor, plasminogen depletion was prevented at the 10 µg/ml M5 concentration, and at 15 and 20 mg/ml, reduced to ~30% and ~60% respectively. Therefore, C1-inhibitor supplementation was effective in promoting the plasma stability of M5 by raising the threshold concentration at which non-specific plasminogen activation occurred.

By contrast, as shown by the last two bars in FIG. 4, C1-inhibitor supplementation had no attenuating effect on plasminogen activation of prouPA at the high concentrations used. At much lower concentrations (2, 4, and 6 µg/ml) of prouPA, however, some attenuation of non-specific plasminogen activation by C1-inhibitor was seen (data not shown).

Fibrin-Specific Clot Lysis as a Function of Supplemental C1-Inhibitor

Clots were formed from 0.2 ml bank plasma by recalcification (35 mM) with the addition of a trace of thromboplastin and incubated at 37° C. for 1 h and overnight at room temperature. The following day, the clots were placed into 2.5 ml of bank plasma and M5 was added at 5 or 10 µg/ml. Lysis was determined by measuring the D-Dimer concentration in plasma samples removed at time intervals (FIG. 5A). The D-Dimer determinations were made independently by Dr. Gregory Gauvin, Mt Auburn Hospital, Cambridge, Mass. using a Beckman ACL 8000 analyzer. After lysis had gone to completion, aprotinin (500 KIU/ml) was added and the fibrinogen concentration determined and compared with that from a baseline sample (FIG. 5B).

The Effects of C1-Inhibitor on Clot Lysis and Fibrin Specificity

The attenuation of non-specific plasminogen activation by C1-inhibitor suggested that fibrin-dependent plasminogen activation and fibrinolysis might also be inhibited. This was anticipated from the clinical experience with PAI-1 in which higher levels have correlated clinically with fibrinolytic resistance, and also from our own laboratory findings in which a PAI-1 dose-dependent inhibition of clot lysis in a plasma milieu by prouPA was previously found (unpublished observations).

FIG. 5A shows representative clot lysis curves measured by the release of D-Dimer from a standardized plasma clot. Lysis induced by 5 or 10 µg/ml of M5 in plasma went to completion in 1½ and 2 hours, respectively, either with (open symbols) or without (closed symbols) C1-inhibitor supplementation (250 µg/ml). No detectable attenuation of the rate of M5-mediated fibrinolysis by the inhibitor was found (experiments done in triplicate), indicating that C1-inhibitor did not inhibit fibrin-dependent plasminogen activation.

By contrast, as seen in FIG. 5B showing the fibrinogen concentrations (as % of baseline) at the end of each clot lysis experiment, fibrinogenolysis was completely inhibited by supplementation with C1-inhibitor (indicated by the + symbol). Therefore, C1-inhibitor completely restored fibrin-specificity to the more rapid clot lysis rate otherwise achievable only at non-specific doses of the activator, i.e., at which fibrin degradation by excess plasmin is the rate-limiting factor.

Since plasmin is the common denominator of all plasminogen-activator mediated lysis, the findings that the fibrin-specific and non-specific rates (when plasmin is in excess), were equivalent are of special interest. They suggest that C1-inhibitor supplementation made a maximal fibrinolysis rate by M5 possible in vitro without sacrificing fibrin-specificity.

Evaluation of C1 Esterase Activity

Since tcM5 was inhibited by the principal inhibitor of C1 esterase, the possibility that it may itself have some intrinsic C1 esterase activity was tested. Equal amounts (10 µg/ml) of tcM5 and tcuPA, adjusted to have equivalent activities against the uPA chromogenic substrate (S2444), were tested against the tripeptide chromogenic substrate Spectrozyme C1-E (480 µg/ml) (FIG. 6A).

Since Complement factor 4 (C4) is the natural substrate for C1 esterase, release of the ~9 kDa peptide from the α-chain of C4 by the activators, using plasmin as a positive control, was also evaluated. A mixture of 10 µl of tcM5, tcuPA, plasmin (10 µg/ml) or buffer were incubated (37° C.) for 6 h with 40 µl C4 (480 µg/ml). Each of the incubation mixtures with C4, except plasmin, also contained aprotinin (100 KIU/ml). At the end of incubation, the mixtures were analyzed by SDS-PAGE under reducing conditions (FIG. 6B).

Figure 6A:
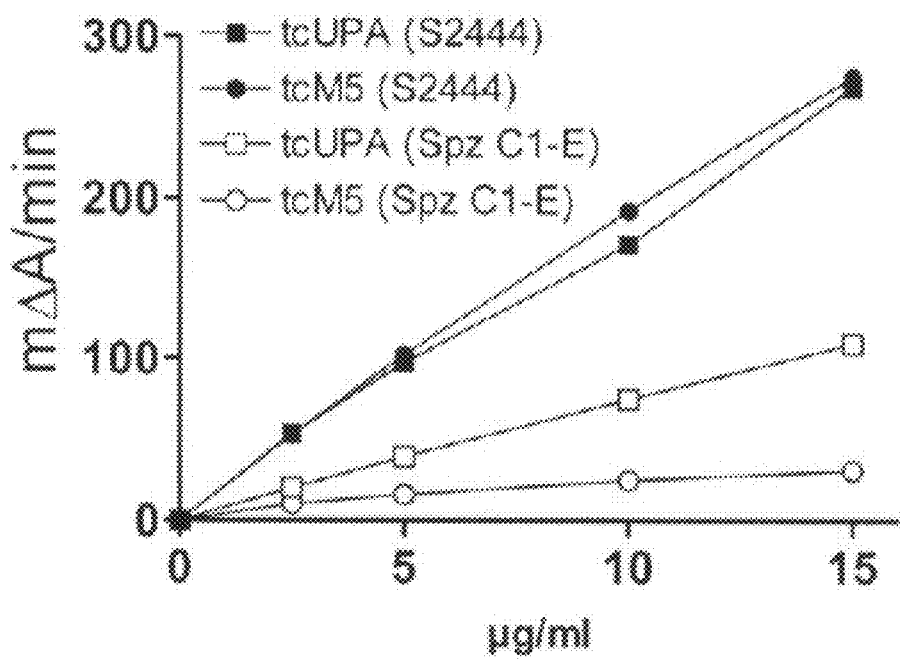
FIG. 6A. Activity against C1 esterase chromogenic substrate (Spectrozyme C1-E) (open symbols) by 0-15 µg/ml of tcuPA or tcM5, amount adjusted to give comparable uPA substrate (S-2444) (solid symbols) activity. As shown, tcM5 had less C1 esterase-like activity than tcuPA. (m$\Delta$A/min is the change in milli-absorbance units (A405) with time, reflecting the rate of conversion of chromogenic substrate to product.)

FIG. 6A shows that at concentrations of tcuPA and tcM5 which were equivalent against uPA chromogenic substrate (solid symbols), tcuPA had more activity against C1 esterase chromogenic substrate than did tcM5 (open symbols). A comparable difference in the same direction was found against the more general substrate, benzoyl-argininyl methyl ester (Sigma) (data not shown).

Figure 6B:
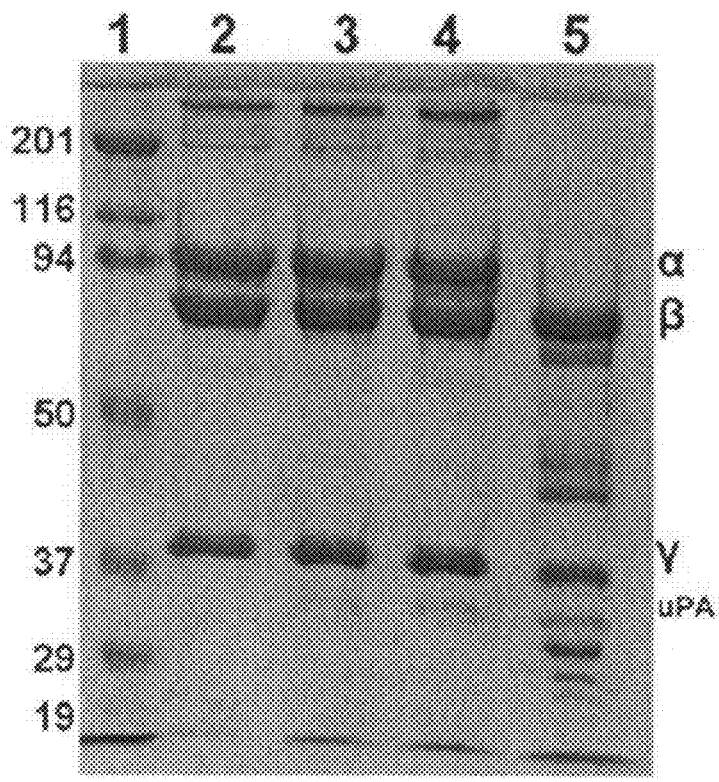
FIG. 6B. Reducing SDS-PAGE (Coomassie stained) of a 6 h incubation mixture of C4 (480 µg/ml) with buffer (lane 2), tcuPA (lane 3), tcM5 (lane 4) or plasmin (lane 5) (10 µg/ml each). Molecular weight markers are in lane 1. The positions of the $\alpha$, $\beta$, and $\gamma$ chains of C4 and of the uPA B-chain (lanes 3 and 4) are shown on the right. A faint band is discernable between the $\alpha$ and $\beta$ chains of C4 in lanes 3 and 4, consistent with a shift of a trace amount of the unchain by release of the anaphylatoxin peptide. By contrast, a gross degradative effect, particularly of the $\alpha$-chain, is seen in lane 5.

FIG. 6B shows an SDS PAGE under reducing conditions of the 6 h incubation mixtures of C4 with the following: buffer (lane 2), tcuPA (lane 3), tcM5 (lane 4) or plasmin (lane 5) (10 µg /ml). A faint band is discernable between the α and β chains of C4 in lanes 3 and 4, consistent with a shift of a trace amount of the α-chain by release of the peptide after a 6 h incubation with a high therapeutic concentration of either tcuPA or tcM5. By contrast, plasmin had a gross degradative effect, particularly of the α-chain.

The effect of plasmin is consistent with those reports in which complement activation and anaphylatoxin generation were found associated with therapeutic thrombolysis. This potentially deleterious side effect of plasmin further underscores the importance of limiting non-specific plasmin generation during fibrinolysis as much as possible.

C1-inhibitor is a major inhibitor of the complement pathway, specifically C1 esterase, but also has a number of other target serine proteases, including Factors XIIa, XIa, kallikrein, and tPA (for review see Ref. 17). The present findings indicate that tcuPA, and especially tcM5, need to be added to the list.

Due to the unusual interaction of tcM5 with C1-inhibitor, the question of whether tcM5 may itself have C1 esterase activity was raised. The activation of the complement system can cause damage to cells. When compared with an equivalent amount of tcuPA, tcM5 had, in fact, less activity against a C1 esterase synthetic substrate (FIG. 6A). Against its natural substrate, C4, both tcuPA and tcM5 at high therapeutic concentrations had a comparable effect consistent with release of a trace amount of anaphylatoxin after a six hour incubation. By contrast, plasmin induced a major degradation (FIG. 6B), consistent with reports of complement activation and anaphylatoxin generation during therapeutic thrombolysis [Bennett et al. (1987), supra]. This data shows that M5 is safe and underscores the importance of limiting non-specific plasmin generation, as has been demonstrated with supplemental C1-inhibitor with M5.

What is claimed is:

1. A method of accelerating the rate of blood clot lysis while preventing fibrinogen degradation in a human patient, comprising:
   a) providing M5 and exogenous C1-inhibitor;
   b) administering to a human patient an amount of M5 sufficient to establish M5 concentrations of 10-15 µg/ml in the plasma of the patient; and
   c) administering, at the same time or before step b), an amount of exogenous C1-inhibitor sufficient to establish a concentration of C1-inhibitor, in the plasma of the patient, that is within the range of 1.5 to 4 times average normal physiological levels;
   wherein non-specific plasminogen activation by M5 is prevented.

2. The method of claim 1, wherein the C1-inhibitor is administered in an amount sufficient to establish a concentration that is within the range of 2 to 3 times average normal physiological levels.

3. The method of claim 1 wherein the C1-inhibitor is mixed in a pharmaceutically acceptable carrier and administered as a bolus.

4. The method of claim 3 wherein the bolus is administered at the same time as M5.

5. The method of claim 1 wherein the C1-inhibitor is either of recombinant origin or of native origin.

6. The method of claim 5 wherein the C1-inhibitor is of recombinant origin and is non-glycosylated or differently glycosylated from the native form.

7. A method of administering a thrombolytic to a human patient without inducing non-specific plasminogen activation, comprising:
   a) providing the thrombolytic M5 and exogenous C1-inhibitor;
   b) administering an amount of exogenous C1-inhibitor sufficient to establish a concentration of C1-inhibitor, in the plasma of the human patient, that is within the range of 1.5 to 4 times average normal physiological levels; and at the same time or after step b)
   c) administering to the human patient an amount of M5 sufficient to establish M5 concentrations of 10-15 µg/ml in the plasma of the human patient; and
   wherein non-specific plasminogen activation by M5 is prevented.

8. The method of claim 7 wherein said C1-inhibitor is administered at the same time as thrombolysis with M5.

9. The method of claim 7, wherein the C1- inhibitor is administered in an amount sufficient to establish a concentration that is within the range of 2 to 3times average normal physiological levels.

10. A method of administering a thrombolytic to a human patient while inhibiting non-specific plasminogen activation, comprising:
   a) providing the thrombolytic M5 and exogenous C1-inhibitor;
   b) administering an amount of exogenous C1-inhibitor sufficient to establish a concentration of C1-inhibitor, in the plasma of the human patient, that is within the range of 1.5 to 4 times average normal physiological levels; and
   c) administering, after or at the same time as step b), to a the human patient an amount of M5 sufficient to establish M5 concentrations of 10-15 µg/ml in the plasma of the patient;
   and wherein non-specific plasminogen activation by M5 is inhibited, without inhibiting clot lysis or fibrin-specific plasminogen activation of M5.

* * * * *